(12) United States Patent
Jones et al.

(10) Patent No.: US 9,358,340 B2
(45) Date of Patent: Jun. 7, 2016

(54) METHOD AND ASSEMBLY FOR A DRUG DELIVERY DEVICE

(75) Inventors: Christopher Jones, Tewkesbury (GB); Robert Veasey, Leamington Spa (GB); Garen Kouyoumjian, Leamington Spa (GB); Catherine Anne MacDonald, Ashby-de-la-Zouch (GB); Michael Jugl, Frankfurt am Main (DE); Gunther Sendatzki, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 51 days.

(21) Appl. No.: 13/496,337

(22) PCT Filed: Sep. 29, 2010

(86) PCT No.: PCT/EP2010/064420
§ 371 (c)(1),
(2), (4) Date: Jul. 31, 2012

(87) PCT Pub. No.: WO2011/039227
PCT Pub. Date: Apr. 7, 2011

(65) Prior Publication Data
US 2012/0289906 A1    Nov. 15, 2012

(30) Foreign Application Priority Data

Sep. 30, 2009  (EP) .................................. 09171758

(51) Int. Cl.
*A61M 5/24*  (2006.01)
*A61M 5/31*  (2006.01)
(Continued)

(52) U.S. Cl.
CPC ............... *A61M 5/24* (2013.01); *A61M 5/3146* (2013.01); *A61M 5/3293* (2013.01);
(Continued)

(58) Field of Classification Search
CPC ..................... A61M 5/31535; A61M 5/31553; A61M 5/31525; A61M 2005/2407; A61M 2005/2488; A61M 5/24; A61M 5/3129; A61M 5/31543; A61M 5/31551
USPC .......... 604/154, 191, 110, 195, 132, 187, 228
See application file for complete search history.

(56) References Cited

U.S. PATENT DOCUMENTS 2,701,566 A  *  2/1955  Krug .............................. 604/154
4,957,490 A  *  9/1990  Byrne et al. .................. 604/197
(Continued)

FOREIGN PATENT DOCUMENTS

EP    0787501  A2    8/1997
EP    0787501  A3    12/1997
(Continued)

OTHER PUBLICATIONS

Gabriel, et al. International Search Report, appended to WO 2005/046770. May 2005.*
(Continued)

*Primary Examiner* — Kami A Bosworth
*Assistant Examiner* — Matthew A Engel
(74) *Attorney, Agent, or Firm* — McDonnell Boehnen Hulbert & Berghoff LLP

(57) ABSTRACT

A method for securing a cartridge (4) in a cartridge holder (3) is provided, the method comprising the steps of
inserting the cartridge (4) into the cartridge holder (3), the cartridge holder (3) having a proximal end and a distal end,
axially displacing the cartridge (4) in a proximal direction with respect to the cartridge holder (3) from a distal initial position to a proximal end position and
securing the cartridge (4) in the end position against displacement in the distal direction with respect to the cartridge holder (3). An assembly for a drug delivery device (1) is provided comprising a cartridge (4), an adjusting member (12, 25, 28, 34) and a cartridge holder (3). The cartridge holder (3) has a distal end and a proximal end. The adjusting member (12, 25, 28, 34) is secured to the cartridge holder (3). The adjusting member (12, 25, 28, 34) holds a distal portion of the cartridge (4) at a distance with respect to a distal portion of the cartridge holder (3).

8 Claims, 3 Drawing Sheets

Figure 1:
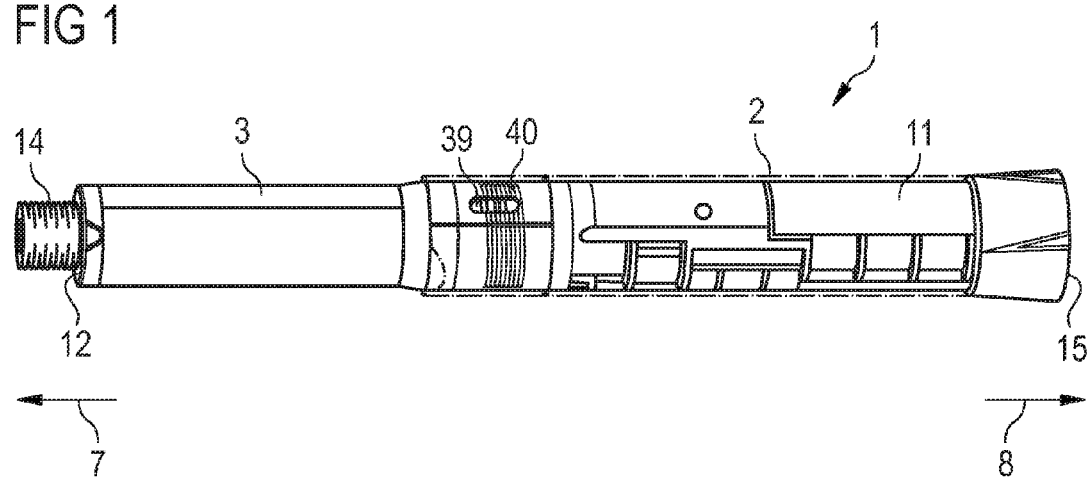

(51) Int. Cl.
  *A61M 5/315* (2006.01)
  *A61M 5/32* (2006.01)
  *A61M 5/34* (2006.01)

(52) U.S. Cl.
  CPC ......... *A61M 5/31555* (2013.01); *A61M 5/3202* (2013.01); *A61M 5/344* (2013.01); *A61M 5/347* (2013.01); *A61M 2005/2407* (2013.01); *A61M 2005/2477* (2013.01); *A61M 2005/2488* (2013.01); *A61M 2205/6045* (2013.01); *A61M 2207/00* (2013.01); *Y10T 29/49826* (2015.01)

(56) References Cited

U.S. PATENT DOCUMENTS

| | | | | |
|---|---|---|---|---|
| 5,125,908 A * | 6/1992 | Cohen | | 604/196 |
| 5,226,895 A * | 7/1993 | Harris | | 604/208 |
| 5,279,585 A * | 1/1994 | Balkwill | | 604/207 |
| 5,300,041 A * | 4/1994 | Haber et al. | | 604/207 |
| 5,403,288 A * | 4/1995 | Stanners | | 604/232 |
| 5,405,326 A * | 4/1995 | Haber et al. | | 604/110 |
| 5,536,253 A * | 7/1996 | Haber et al. | | 604/110 |
| 5,542,927 A * | 8/1996 | Thorne et al. | | 604/110 |
| 5,584,815 A | 12/1996 | Pawelka et al. | | |
| 5,593,391 A * | 1/1997 | Stanners | | 604/232 |
| 5,611,786 A * | 3/1997 | Kirchhofer et al. | | 604/240 |
| 5,626,566 A * | 5/1997 | Petersen et al. | | 604/208 |
| 5,695,472 A * | 12/1997 | Wyrick | | 604/136 |
| 5,879,627 A * | 3/1999 | Tanihata | | 422/67 |
| 6,004,297 A * | 12/1999 | Steenfeldt-Jensen et al. | | 604/207 |
| 6,042,571 A * | 3/2000 | Hjertman et al. | | 604/208 |
| 6,235,004 B1 * | 5/2001 | Steenfeldt-Jensen et al. | | 604/207 |
| 6,241,709 B1 * | 6/2001 | Bechtold et al. | | 604/207 |
| 6,319,234 B1 * | 11/2001 | Restelli et al. | | 604/198 |
| 6,656,163 B1 * | 12/2003 | Marshall et al. | | 604/198 |
| 6,663,602 B2 | 12/2003 | Møller | | 604/211 |
| 6,899,699 B2 * | 5/2005 | Enggaard | | 604/246 |
| 7,195,616 B2 * | 3/2007 | Diller et al. | | 604/224 |
| 7,291,132 B2 * | 11/2007 | DeRuntz et al. | | 604/207 |
| 7,297,135 B2 * | 11/2007 | Jeffrey | | 604/110 |
| 7,419,478 B1 * | 9/2008 | Reilly et al. | | 604/241 |
| 7,553,293 B2 * | 6/2009 | Jensen et al. | | 604/110 |
| 7,736,333 B2 * | 6/2010 | Gillespie, III | | 604/110 |
| 7,771,398 B2 * | 8/2010 | Knight et al. | | 604/208 |
| 7,918,832 B2 * | 4/2011 | Veasey et al. | | 604/207 |
| 8,376,998 B2 * | 2/2013 | Daily et al. | | 604/136 |
| 2003/0233070 A1 * | 12/2003 | De La Serna et al. | | 604/141 |
| 2006/0178638 A1 * | 8/2006 | Reynolds | | 604/191 |
| 2008/0015511 A1 * | 1/2008 | Veasey et al. | | 604/187 |
| 2008/0051729 A1 | 2/2008 | Cheng | | |
| 2012/0283662 A1 * | 11/2012 | MacDonald et al. | | 604/236 |

FOREIGN PATENT DOCUMENTS

| | | |
|---|---|---|
| EP | 0897728 A1 | 2/1999 |
| EP | 1923083 A1 | 5/2008 |
| JP | H11-276583 | 10/1999 |
| JP | 2003-531646 | 10/2003 |
| JP | 2007-502146 | 2/2007 |
| JP | 2008-161673 | 7/2008 |
| WO | 90/09202 | 8/1990 |
| WO | 01/52925 | 7/2001 |
| WO | 2005/018721 | 3/2005 |
| WO | 2006063472 A1 | 6/2006 |
| WO | 2009146996 A1 | 12/2009 |

OTHER PUBLICATIONS

Kouyoumjian, et al. International Search Report, appended to WO 2011/039233. Apr. 2011.*
Form PCT/IPEA/416, Notification of Transmittal of the International Preliminary Report on Patentability.
Japanese Office Action for JP App. No. 2012-531391, mailed Jun. 24, 2014.
Communication from European Patent Office regarding European Patent Application No. 10763647.3-1660 dated Jun. 18, 2014.
Communication issued in European Patent Application No. 10763647.3 dated May 27, 2015.

* cited by examiner

METHOD AND ASSEMBLY FOR A DRUG DELIVERY DEVICE

CROSS REFERENCE TO RELATED APPLICATIONS

The present application is a 35 U.S.C. 371 National Application of PCT/EP2010/064420 filed Sep. 29, 2010, which claims priority to European Patent Application No. 09171758.7, filed Sep. 30, 2009, the entire contents of which are incorporated entirely herein by reference.

This disclosure relates to a method for securing a cartridge in a cartridge holder. The disclosure further relates to an assembly for a drug delivery device.

In a drug delivery device often a piston within a cartridge containing a plurality of doses of a drug is displaced with respect to the cartridge in a distal direction by a piston rod. Thereby, a dose of the drug may be expelled from the cartridge.

Drug delivery devices are described in documents EP 1 923 083 A1 and WO 2006/063472 A1.

It is an object of the present disclosure to facilitate provision of an improved drug delivery device, for example a device with high dose accuracy.

This object may be achieved by the subject matter of the independent claims. Further features are the subject matter of the dependent claims.

According to one aspect a method for securing a cartridge in a cartridge holder is provided. The cartridge may be inserted into the cartridge holder. The cartridge holder may have a proximal end and a distal end. The cartridge may be axially displaced in a proximal direction with respect to the cartridge holder from a distal initial position to a proximal end position. The cartridge may be secured in the end position, preferably secured against displacement in the distal direction with respect to the cartridge holder.

Another aspect relates to an assembly for a drug delivery device. The assembly comprises a cartridge. The assembly comprises an adjusting member. The assembly comprises a cartridge holder. The cartridge holder may have a distal end and a proximal end. The adjusting member may be secured to the cartridge holder. The adjusting member may hold a distal portion of the cartridge at a distance with respect to a distal portion of the cartridge holder. The distal portion of the cartridge holder may be adapted to mechanically cooperate, in particular to abut, with the distal portion of the cartridge. Said cooperation may be prevented by means of the adjusting member.

Another aspect relates to a drug delivery device. The drug delivery device preferably comprises the assembly as described above. The cartridge may contain a drug. A piston may be, preferably movably retained in the cartridge. The drug delivery device may comprise a housing. A piston rod may be retained in the housing. The piston rod may be operable to be displaced with respect to the housing in the distal direction. The piston rod may be prevented from being displaced with respect to the housing in the proximal direction. The piston rod may be configured to displace the piston distally with respect to the cartridge for dispensing a dose of the drug. The piston rod may abut the piston when the drug delivery device is in the condition as originally supplied from the manufacturer.

The drug delivery device may be an injection device. The drug delivery device may be a pen-type device, e.g. a pen-type injector. The cartridge may hold a plurality of doses of a drug. Preferably, the drug comprises a liquid medication, such as long-acting, short-acting insulin, heparin and/or growth hormones. The drug delivery device may be designed such that it may accommodate cartridges of different sizes. Additionally or alternatively, the drug delivery device may be designed such that it may accommodate cartridges of different shapes. Variations in shape and/or size of the cartridge may be compensated by the adjusting member. Preferably, the cartridge has an outlet at its distal end. A septum may seal the outlet. The distal end of the cartridge holder may be the end which is closest to the outlet of the cartridge when the cartridge is arranged within the cartridge holder.

After having checked whether components of the drug delivery device have been assembled properly, e.g. whether the piston and the piston rod abut, the cartridge may be secured in the cartridge holder in the proximal end position. Preferably, the cartridge may be secured in the cartridge holder in the proximal end position by means of the adjusting member being secured to the cartridge holder.

Thereby, the adjusting member may act as a distance piece for keeping the distance between the cartridge and the cartridge holder, in particular between the distal portion of the cartridge and the distal portion of the cartridge holder, when the cartridge is in the proximal end position. In this way, accidental distal displacement of the cartridge with respect to the cartridge holder and, consequently, accidental displacement of the piston with respect to the piston rod may be prevented.

User-operated steps for adjusting the cartridge with respect to the cartridge holder and for bringing the piston rod into abutment with the piston may be redundant. In particular, any set-up step to be carried out by a user for removing assembly tolerances in order to guarantee a high dose accuracy may be avoided. Hence, a user-friendly and easily handled drug delivery device may be provided. In addition, the drug delivery device may provide a high dose accuracy as play between the piston rod and the piston may be completely removed once the cartridge is secured in the proximal end position, e.g. when the device is supplied to the user. Underdosing, which may have fatal or lethal consequences for the user, may be prevented in this way.

According to an embodiment, a method for assembling a drug delivery device is provided. For this purpose, the cartridge is provided. The cartridge may contain the drug. The piston may be retained within the cartridge. Also, the cartridge holder is provided. Furthermore, the housing is provided. The piston rod may be retained in the housing. The piston rod may be operable to displace the piston with respect to the cartridge. Firstly, the cartridge holder may be secured to the housing, such that the piston is arranged at a distance from the piston rod. Afterwards, the cartridge may be secured in the cartridge holder according to the method described above. When the cartridge is axially displaced in the proximal direction with respect to the cartridge holder away from the initial position, the piston may be displaced towards the piston rod.

The piston may seal the cartridge proximally. Preferably, the cartridge is securable in the cartridge holder in different proximal end positions. In an initial assembly state of the drug delivery device there may be a gap between the piston rod and the piston. The size of the gap may vary due to manufacturing tolerances. However, when delivering the drug, the gap between the piston rod and the piston may reduce the dose accuracy, because the piston rod has to close the gap before the piston may be advanced and drug may be expelled. Due to different proximal end positions of the cartridge differently sized gaps between the piston rod and the piston may be compensated and hence, high dose accuracy may be guaranteed. After the cartridge has been secured in the proximal end position the drug delivery device may be in a ready for delivery condition.

According to an embodiment, during the axial displacement of the cartridge with respect to the cartridge holder it is detected whether the piston abuts the piston rod. If the piston abuts the piston rod the axial displacement of the cartridge with respect to the cartridge holder may be stopped in the end position which may be defined by the piston abutting the piston rod. The cartridge may be secured against displacement in the distal direction with respect to the cartridge holder.

In this way, permanent abutment of the piston rod and the piston may be facilitated in the delivery condition. User-operated steps, such as a priming step, for minimizing the gap between the piston rod and the piston may be redundant. Hence, an easily handled and user friendly device may be achieved.

According to an embodiment, the adjusting member is displaced in the proximal direction with respect to the cartridge holder for axially displacing the cartridge.

Due to displacing the adjusting member proximally the cartridge may be displaced towards the proximal end position and hence, the gap between the piston rod and the piston may be minimized.

According to an embodiment, the adjusting member is irreversibly fixed to the cartridge holder.

In this way, the cartridge may be permanently secured in the cartridge holder against distal displacement with respect to the cartridge holder. Consequently, permanent abutment of the piston rod and the piston may be facilitated.

According to an embodiment, the adjusting member is reversibly fixed to the cartridge holder.

This may be especially applicable for re-usable drug delivery devices.

According to an embodiment, the adjusting member extends from the inside of the cartridge holder to the outside of the cartridge holder. An outer surface of the adjusting member which is accessible from outside of the cartridge holder may be provided for attaching a needle unit to the adjusting member.

Attaching the needle unit to the adjusting member may for example serve for exerting a proximally directed force to the adjusting member, thereby displacing the adjusting member and the cartridge proximally with respect to the cartridge holder and, thus, reducing or even closing the gap between the piston rod and the piston. A user-operated priming step for closing the gap between the piston rod and the piston during the first actuation of the drug delivery device for setting and delivering a dose may be avoided.

According to an embodiment, the outer surface of the adjusting member is provided with a needle thread.

This may help for threadedly attaching the needle unit to the adjusting member. The adjusting member may, in particular, be configured as a needle hub.

According to an embodiment, the adjusting member comprises an outer thread. The outer thread may be adapted to engage an inner thread of the cartridge holder.

In this way, the adjusting member may be, irreversibly or reversibly, securable to the cartridge holder such that the adjusting member may keep the cartridge in the proximal end position.

According to an embodiment, the adjusting member is arranged in the distal portion of the cartridge holder. According to an embodiment, the distal portion of the cartridge comprises an outwardly directed shoulder portion. The distal portion of the cartridge holder may comprise an inwardly directed shoulder portion or flange portion. The outwardly directed portion may be of suitable dimension to abut the inwardly directed portion. The adjusting member may prevent an abutment of the outwardly directed portion and the inwardly directed portion.

The distal portion of the cartridge holder may be adapted to mechanically cooperate, in particular to abut, with the distal portion of the cartridge. A distance between the distal portion of the cartridge and the distal portion of the cartridge holder may be kept by means of the adjusting member. Consequently, accidental displacement of the cartridge in the distal direction with respect to the cartridge holder may be prevented.

Of course, features relating to different aspects or embodiments described above and below may be combined with each other.

Further features and refinements become apparent from the following description of exemplary embodiments in connection with the accompanying figures.

Figure 2:
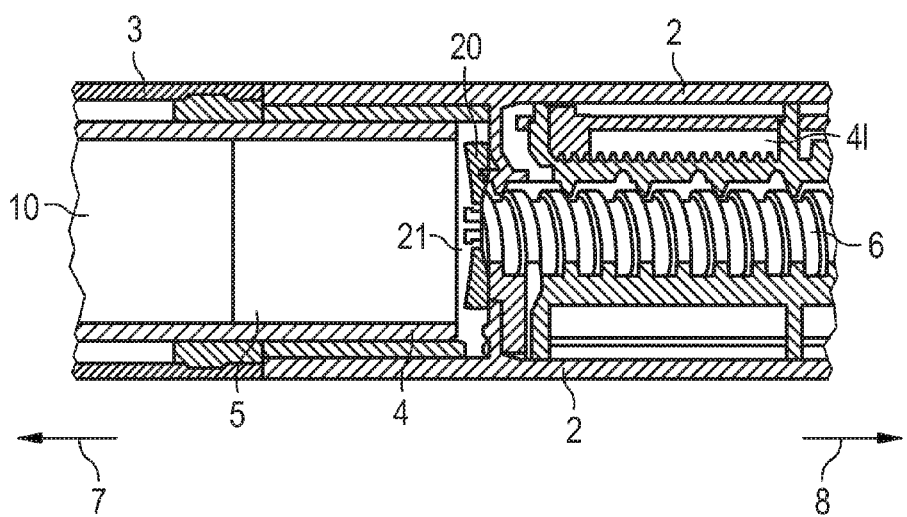
Figure 3:
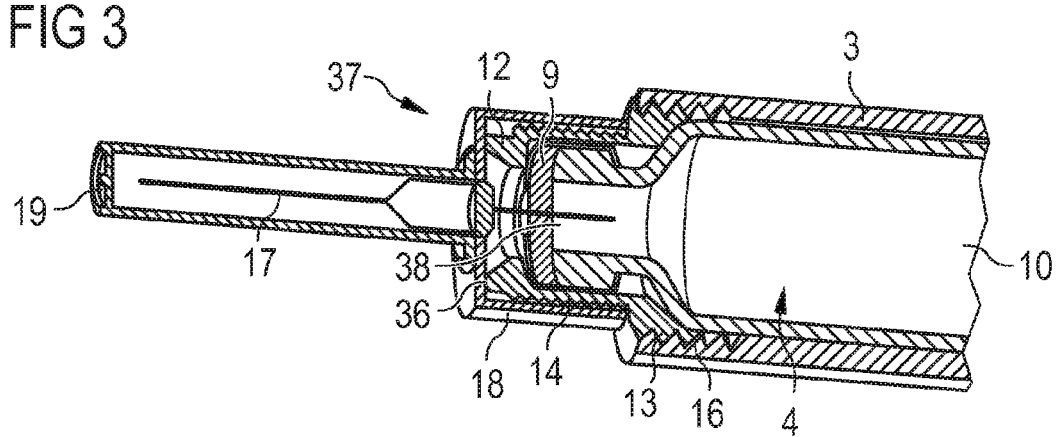
Figure 4:
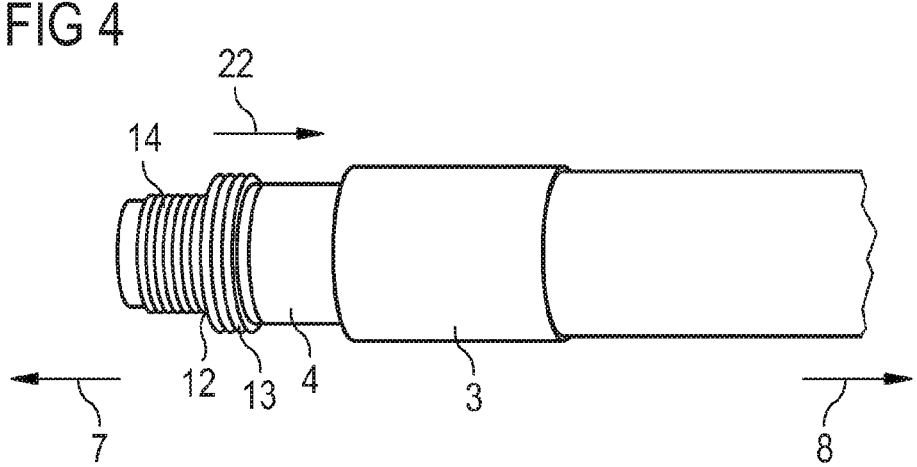
Figure 5:
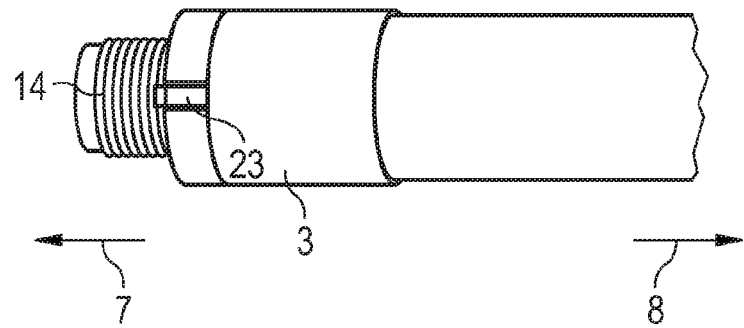
Figure 6A:
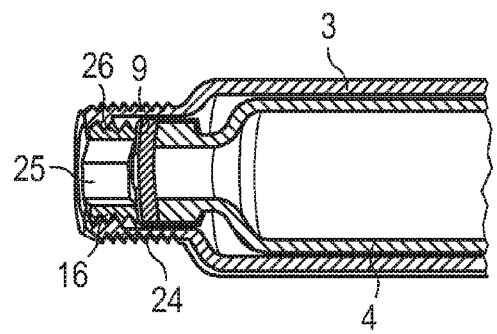
Figure 6B:
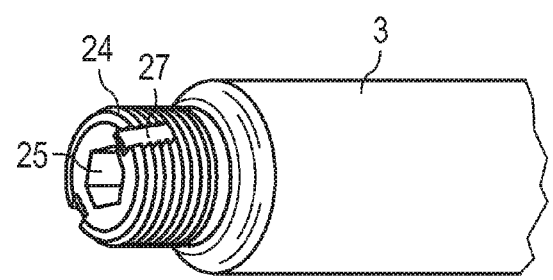
Figure 7:
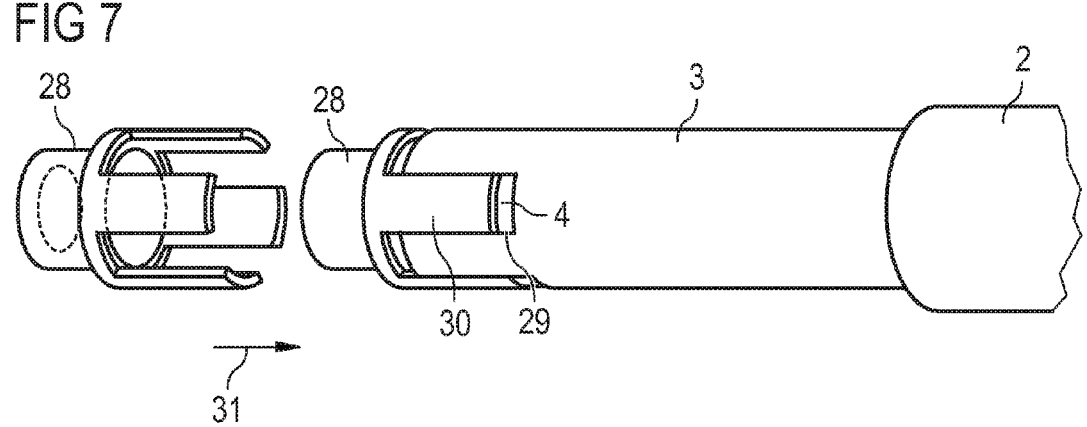
Figure 8:
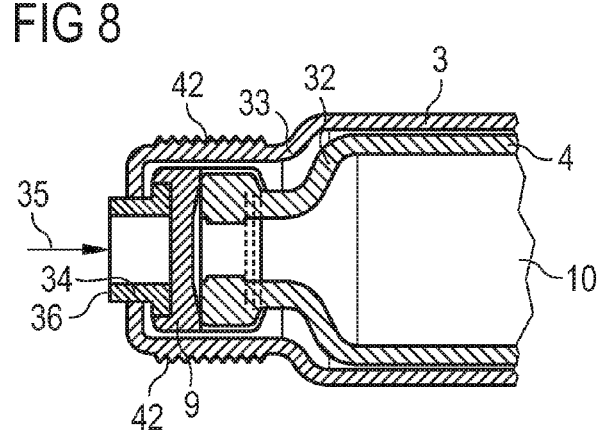

FIG. 1 schematically shows a sectional side view of an exemplary drug delivery device, FIG. 2 schematically shows a sectional view of a part of the drug delivery device of FIG. 1, FIG. 3 schematically shows a perspective inner sectional view of a part of the drug delivery device of FIG. 1 for a first embodiment, FIG. 4 schematically shows an outer view of the part of the drug delivery device of FIG. 3 in an unassembled condition, FIG. 5 schematically shows an outer view of the part of the drug delivery device of FIG. 3 in an assembled condition, FIG. 6 schematically shows a perspective inner view of a part of the drug delivery device of FIG. 1 for a second embodiment on the basis of a sectional view in FIG. 6A and an oblique view in FIG. 6B, FIG. 7 schematically shows an outer view of a part of the drug delivery device of FIG. 1 for a third embodiment, FIG. 8 schematically shows an inner view of a part of the drug delivery device of FIG. 1 for a fourth embodiment.

Like elements, elements of the same kind and identically acting elements may be provided with the same reference numerals in the figures.

In FIG. 1 a drug delivery device 1 is shown. The drug delivery device 1 comprises a housing 2. The drug delivery device 1 comprises a cartridge 4 (not explicitly shown in FIG. 1, see FIG. 2). The cartridge 4 is retained within a cartridge holder 3. The cartridge holder 3 stabilizes the cartridge 4 mechanically.

The cartridge 4 contains a drug 10 (see FIG. 2), preferably a plurality of doses of the drug 10. The drug 10 is preferably a liquid medication, for example comprising insulin, like short-acting or long-acting insulin, heparin or growth hormones.

The term "drug", as used herein, preferably means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)-4-des Pro36, des Pro37 Exendin-4(1-39)-NH2,
H-(Lys)-5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
H-(Lys)-6-des Pro36 [Asp28] Exendin-4(1-39)-Lys6-NH2,
des Asp28 Pro36, Pro37, Pro38Exendin-4(1-39)-NH2,
H-(Lys)-6-des Pro36, Pro38 [Asp28] Exendin-4(1-39)-NH2, H-Asn-(Glu)5des Pro36, Pro37, Pro38 [Asp28] Exendin-4(1-39)-NH2,
des Pro36, Pro37, Pro38 [Asp28] Exendin-4(1-39)-(Lys) 6-NH2,
H-(Lys)-6-des Pro36, Pro37, Pro38 [Asp28] Exendin-4(1-39)-(Lys)6-NH2,
H-Asn-(Glu)-5-des Pro36, Pro37, Pro38 [Asp28] Exendin-4(1-39)-(Lys)6-NH2,
H-(Lys)-6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)-6-des Pro36, Pro37, Pro38 [Trp(O2)25, Asp28] Exendin-4(1-39)-NH2,
H-Asn-(Glu)-5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)-6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)-6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)-6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)-6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)-6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)-6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The cartridge 4 may comprise an outlet 38 (not explicitly shown in FIG. 1, see FIG. 3). The drug 10 can be dispensed from the cartridge 4 through the outlet 38. A septum 9 (see FIG. 3) may seal the outlet 38. The septum 9 may be made of an elastically deformable material.

The drug delivery device 1 comprises a piston rod 6 (see FIG. 2). The device 1 comprises a piston 5 (not explicitly shown in FIG. 1, see FIG. 2). The drug delivery device 1 comprises a needle hub 12. By means of the needle hub 12a needle unit 37 (see FIG. 3) may be secured to the drug delivery device 1. The needle unit 37 may comprise for example a needle 17 covered by a needle mount and a needle holder 18. The septum 9 may be pierceable by the needle 17 for dispensing a dose of the drug 10 via the needle extending through the outlet 38. The needle hub 12 may be integrated in the cartridge holder 3 or may be a separate component.

The drug delivery device 1 and the housing 2 have a distal end and a proximal end. The distal end of the device 1 is indicated by arrow 7. The distal end designates that end of the drug delivery device 1 or a component thereof which is closest to a dispensing end of the drug delivery device 1. The proximal end of the device 1 is indicated by arrow 8. The proximal end designates that end of the device 1 or a component thereof which is furthest away from the dispensing end of the device 1.

The cartridge holder 3 may be securable, preferably releasably securable, to the housing 2. Preferably, the cartridge holder 3 is releasably secured to the housing 2 by means of a threaded connection 40. The threaded connection 40 may be visible and/or accessible from the outside via aperture 39 in the housing 2. Alternatively, the cartridge holder 3 may be non-releasably, i.e. permanently, secured to the housing 2. The cartridge holder 3 may be glued or welded to the housing 2 for permanently securing the cartridge holder 3 to the housing 2.

The housing 2 may be designed to enable a safe and comfortable handling of the drug delivery device 1. The housing 2 may be configured to house, fix, protect and guide inner components of the drug delivery device 1, e.g. the piston rod 6. Preferably, the housing 2 limits or prevents the exposure of the inner components to contaminants such as liquid, dirt or dust. The housing 2 may be a unitary or a multipart component. The housing 2 may comprise a tubular or a cylindrical shape, as shown in FIG. 1. Alternatively, the housing 2 may comprise a non-tubular shape.

The piston rod 6 may operate through the housing 2 of the drug delivery device 1. The piston rod 6 may be designed to transfer axial movement through the drug delivery device 1, for example for the purpose of delivering the drug 10. A bearing member 20 (see FIG. 2) may be positioned at the distal end of the piston rod 6. The bearing member 20 may facilitate interaction of the piston 5 and the piston rod 6. The bearing member 20 may be axially locked to the piston rod 6. The piston rod 6 is preferably rotatable with respect to the bearing member 20.

The piston 5 may be slideably retained within the cartridge 4 of the drug delivery device 1. Preferably, the piston 5 comprises a resilient material. The piston 5 is movable with respect to the cartridge 4. The piston 5 may seal the cartridge 4 proximally. Movement of the piston 5 in the distal direction with respect to the cartridge 4 causes the drug 10 to be dispensed from the cartridge 4 through the outlet 38.

In an initial assembly state of the drug delivery device 1 there may be a gap (see gap 21, FIG. 2) between the piston rod 6 and the piston 5. The size of the gap 21 may vary due to manufacturing tolerances. However, in the delivery condition a gap 21 between the piston rod 6 and the piston 5 may reduce the dose accuracy, because the piston rod 6 has to close the gap 21 before the piston 5 may be advanced and the drug 10 may be expelled.

The drug delivery device 1 may comprise a drive mechanism (not explicitly shown in FIG. 1, see drive mechanism 41 in FIG. 2). The drive mechanism may be retained within the housing 2. When delivering a dose of the drug 10, the piston rod 6 may be displaced in the distal direction with respect to the housing 2 due to operation of the drive mechanism. The piston rod 6 may be prevented from displacement in the proximal direction during a dose setting operation. A dose member 11 may be part of the drive mechanism. The user may displace the dose member 11 in the proximal direction with respect to the housing 2 for setting a dose of the drug 10. Afterwards, the user may displace the dose member 11 in the distal direction with respect to the housing 2 for delivering the set dose of the drug 10. A dose button 15 may be integrally formed with the dose member 11 or may be connected to the dose member 11. The dose button 15 may be secured against rotational movement with respect to the dose member 11. The user may pull the dose button 15 in the proximal direction for setting a dose of the drug 10.

The drug delivery device 1 may be a pen-type device, in particular a pen-type injector. The device 1 may be a disposable device, for example. The device may be configured to dispense fixed doses, i.e. non-user variable doses, e.g. constant doses, of the drug or variable, preferably user-settable doses of the drug 10. Especially for a fixed dose device it may be crucial that there is no gap 21 between the piston rod 6 and the piston in the delivery condition as a gap 21 may reduce dose accuracy as mentioned above, in particular when delivering the first dose. The drug delivery device 1 may be a manually, in particular a non-electrically, driven device.

FIG. 2 schematically shows a sectional view of a part of the drug delivery device of FIG. 1. In particular, FIG. 2 shows the device 1 before assembly of the device 1 is completed, e.g. when the device 1 is in the initial assembly condition as mentioned in connection with the description of FIG. 1. Hence, a considerable gap 21 is shown between the piston rod 6 and the piston 5. Said gap 21 has to be minimized for achieving high dose accuracy of the drug delivery device 1 and hence, for preventing underdosing, without an additional set-up step.

FIG. 3 schematically shows a perspective inner view of a part of the drug delivery device 1 of FIG. 1 for a first embodiment. In particular, FIG. 3 shows a distal end section of the drug delivery device 1.

FIG. 4 schematically shows an outer view of the part of the drug delivery device of FIG. 3 in an unassembled condition.

For assembling the drug delivery device 1, the following steps may be performed:

In a first step the cartridge 4 containing the drug 10 is provided. The piston 5 is retained within the cartridge 4. The cartridge holder 3 is provided. The cartridge holder 3 may have a proximal end and a distal end.

Also, the housing 2 is provided. The piston rod 6 is expediently retained in the housing 2. The piston rod 6 may be operable to displace the piston 5 with respect to the cartridge 4 as described in conjunction with the description of FIG. 1.

In a second step the cartridge 4 may be inserted into the cartridge holder 3. The cartridge holder 3 may be secured to the housing 2. Preferably, the cartridge holder 3 is releasably secured to the housing 2 for example by means of threaded connection 40 as mentioned above.

The cartridge holder 3 may be secured to the housing 2 such that the piston 5 may be arranged at a distance from the piston rod 6 when the device 1 was finished. Hence, there is gap 21 between the piston 5 and the piston rod 6. As mentioned previously the size of the gap 21 may vary.

In a third step the cartridge 4 may be secured in the cartridge holder 3. For this purpose, the position of the cartridge 4, may be adjusted with respect to the cartridge holder 3, e.g. the cartridge 4 may be axially displaced in the proximal direction with respect to the cartridge holder 3 away from a distal initial position to a proximal end position (see arrow 22 in FIG. 4). Thereby, the piston 5 may be displaced towards the piston rod 6, i.e. the gap 21 between the piston 5 and the piston rod 6 may be minimized or closed.

The proximal displacement distance of the cartridge 4 with respect to the cartridge holder 3 towards the proximal end position may thus depend on the size of the gap 21.

During the proximal displacement of the cartridge 4 with respect to the cartridge holder 3 a further step may be performed to detect whether the piston 5 abuts the piston rod 6. Said step may comprise detecting the force or torque necessary to displace the cartridge 4 proximally with respect to cartridge holder 3. Contact between the piston 5 and the piston rod 6 may be detected for example by determining whether the force or torque exceeds a predetermined value. Additionally or alternatively, said step may comprise measurements of the position of the piston 5 and the position of the piston rod 6 in order to calculate the axial position of the piston 5 relative to the piston rod 6, and hence, of the cartridge 4, suitable for abutment between the piston 5 and the position of the piston rod 6.

When the piston 5 abuts the piston rod 6, proximal displacement of the cartridge 4 with respect to the cartridge holder 3 may be stopped. When the piston 5 abuts the piston rod 6 the cartridge 4 may be positioned in the proximal end position. In the proximal end position, the gap 21 between the piston 5 and the piston rod 6 may be removed. In this way, a user-operated priming step which may be necessary for ordinary drug delivery devices 1 for closing the gap 21 between the piston rod 6 and the piston 5 may be redundant. Thus, high dose accuracy may be guaranteed already when the device 1 is supplied to the user. Preferably, adjustment of the axial position of the cartridge 4 relative to the cartridge holder 3 to take up the manufacturing tolerances may be made only once, i.e. during manufacture, in particular during assembly, of the device 1. This is particular relevant for a disposable device.

In a last step, the cartridge 4 may be, releasably or non-releasably, secured in the proximal end position against displacement in the distal direction with respect to the cartridge holder 3. In this way, the piston rod 6 and the piston 5 may be kept in abutment. There may be a plurality of different axial securing positions for the cartridge 4. The different securing positions may depend on the size of the gap 21 between the piston 5 and the piston rod 6.

The cartridge 4 may for example be releasably secured in the proximal end position in the cartridge holder 3 by means of snap-fit elements. This may be especially applicable for a re-usable drug delivery device 1 as the cartridge 4 may be easily unsecured from the cartridge holder 3 for introducing a replacement cartridge into the drug delivery device 1. Alternatively, the cartridge 4 may be permanently secured, for example glued, in the cartridge holder 3. Unsecuring the cartridge 4 from the cartridge holder 3 and out of the proximal end position may thus be effectively prevented. This may be especially applicable for disposable drug delivery devices 1.

Additionally or alternatively, an adjusting member may be used for securing the cartridge 4 in the proximal end position in the cartridge holder 3.

The adjusting member may comprise a needle hub 12, for example. Of course, other adjusting members apart from needle hub 12 may be possible, for example a needle insert.

The needle hub 12 may be arranged at a distal end portion of the cartridge holder 3. The needle hub 12 may be, at least partly, arranged inside the cartridge holder 3, for example. For introducing the needle hub 12 at least partly into the cartridge holder 3, the needle hub 12 may be guided from the outside of the cartridge holder 3 to the inside of the cartridge holder 3 via a distal opening in the cartridge holder 3, for example (see also FIG. 6). The needle hub 12 may extend from the inside of the cartridge holder 3 to the outside of the cartridge holder 3.

The needle hub 12 may comprise an outer surface 36. Outer surface 36 may be accessible from the outside of the cartridge holder 3. The outer surface 36 may be suitable for securing a needle to the drug delivery device 1. The outer surface 36 may comprise a thread 14. The outer surface 36, in particular thread 14, may be provided for attaching a needle unit 37 to the needle hub 12. Needle unit 37 may be attached to the needle hub 12 by means of mechanical cooperation of outer thread 14 and an inner thread (not explicitly shown) of the needle unit 37. A cap 19 may be arranged at the distal end portion of the needle unit 37. The cap 19 may protect the needle 17 from exposure to dust, for example.

A proximal end portion of the needle hub 12 may abut the distal end of the cartridge 4. For attaching the needle hub 12 to the cartridge holder 3 the needle hub 12 may be displaced in the proximal direction with respect to the cartridge holder 3. Preferably, simultaneously the cartridge 4 is axially displaced towards the proximal end position as indicated by arrow 22 in FIG. 4.

Alternatively, the cartridge 4 may have been displaced to the proximal end position before the needle hub 12 is arranged at the distal end portion of the cartridge holder 3 (see embodiment in FIG. 7). In this case common proximal displacement of the needle hub 12 and the cartridge 4 for displacing the cartridge 4 towards the proximal end position may be redundant.

Once the cartridge 4 is in the proximal end position the needle hub 12 may be secured against displacement with respect to the cartridge holder 3 in the distal direction. The needle hub 12 may be in abutment with the cartridge 4. Hence, the cartridge 4 may be secured in the proximal end position against displacement in the distal direction with respect to the cartridge holder 3 by means of the needle hub 12.

The needle hub 12 may be reversibly fixed to the cartridge holder 3, for example. For this purpose, the needle hub 12 may comprise a further outer thread 13. Thread 13 may be arranged at the proximal end portion of the needle hub 12. The cartridge holder 3 may comprise an inner thread 16. Inner thread 16 may be arranged at the distal end portion of the cartridge holder 3. Due to mechanical cooperation of the outer thread 13 and the inner thread 16 the needle hub 12 may be secured to the cartridge holder 3.

Alternatively, the needle hub 12 may be irreversibly fixed to the cartridge holder 3. The needle hub 12 may be irreversibly fixed to the cartridge holder 3 by means of a permanently locked screw thread, for example. The needle hub 12 may be irreverseably fixed to the cartridge holder 3 by means of deformation of at least a portion of the outer thread 13 or a portion of the inner thread 16 or deformation of at least a portion of outer thread 13 and inner thread 16, for example (see also connection 23 in FIG. 5).

Additionally or alternatively, the needle hub 12 may be irreversibly fixed to the cartridge holder 3 by means of applying an adhesive to at least a portion of outer thread 13 or a portion of inner thread 16 or applying an adhesive to at least a portion of outer thread 13 and inner thread 16, for example.

Once fixed to the cartridge holder 3 the needle hub 12 may hold the distal portion of the cartridge 4 at a distance with respect to the distal portion of the cartridge holder 3. Hence, the needle hub 12 may ensure that the cartridge 4 may not be accidentally distally displaceable out of the proximal end position with respect to the cartridge holder 3. Thus, the needle hub 12 may ensure that the piston 5 is held in abutment with the piston rod 6. In this way, a high dose accuracy is guaranteed and underdosing may be prevented.

As described above reducing the gap 21 between the piston 5 and the piston rod 6 until the piston 5 abuts the piston rod 6, may be performed automatically while assembling the drug delivery device 1. Thus, high dose accuracy may be guaranteed once the drug delivery device 1 is assembled. No user-operated step, e.g. a priming step, may be required to minimize the distance between the piston 5 and the piston rod 6. In this way, an easily handled device 1 providing high safety for the user is achieved.

The above described method may be especially suitable for assembling fixed dose drug delivery devices 1. Alternatively, the method may be applicable for assembling variable dose drug delivery devices 1.

FIG. 5 schematically shows an outer view of the part of the drug delivery device of FIG. 3 in an assembled condition. In particular, FIG. 5 shows the drug delivery device near the end of assembly, e.g. when the cartridge 4 has been positioned, and preferably secured, in the proximal end position.

For keeping the piston 5 and the piston rod 6 in abutment, i.e. for keeping the cartridge 4 in the proximal end position, the needle hub 12 may be irreversibly secured against displacement with respect to the cartridge holder 3. The needle hub 12 may be secured to the cartridge holder 3 by means of connection region 23. Connection region 23 may be suitable for snap-fitting or clamping the needle hub 12 to the cartridge holder 3. Additionally, connection region 23 may facilitate applying force or heat to the needle hub 12, in particular to thread 13, such that at least a portion of thread 13 may be spoilt, for example deformed, for irreversably securing the needle hub 12 to the cartridge holder 3. Connection region 23 may hence provide for a permanently locked screw thread.

FIG. 6 schematically shows a perspective view of a part of the drug delivery device 1 of FIG. 1 for a second embodiment on the basis of a sectional view in FIG. 6A and an oblique view in FIG. 6B.

The adjusting member may comprise a needle insert 25 in this case. The needle insert 25 may be arranged at the distal end portion of the cartridge holder 3. The needle insert 25 may be arranged inside the cartridge holder 3. The needle insert 25 may be guided from the outside of the cartridge holder 3 to the inside of the cartridge holder 3 via a distal opening in the cartridge holder 3, for example. The needle insert 25 may comprise an outer thread 26.

The needle insert 25 may be secured against distal displacement with respect to the cartridge holder 3 by means of mechanical cooperation of outer thread 26 and inner thread 16 of the cartridge holder 3 (see FIG. 6A). In this way, the needle insert 25 may hold the distal portion of the cartridge 4 at a distance with respect to the distal portion of the cartridge holder 3 when the cartridge 4 is in the proximal end position. The distance may be such that the piston 5 abuts the piston rod 6 as described previously.

The needle insert 25 may be irreversibly or reversibly secured to the cartridge holder 3 by means of connection region 27 (see FIG. 6B). As described above connection region 27 may facilitate applying force or heat to the threaded connection between the needle insert 25 and the cartridge holder 3, in particular to outer thread 26 and inner thread 16, such that at least a portion of the threaded connection may be spoilt. Additionally or alternatively, the needle insert 25 may be glued into the cartridge holder 3.

The cartridge holder 3 may comprise an outer thread 24. Outer thread 24 may be provided for attaching needle unit 37 to the distal end portion of the cartridge holder 3, for example.

FIG. 7 schematically shows an outer view of a part of the drug delivery device of FIG. 1 for a third embodiment.

In particular, FIG. 7 shows the drug delivery device during assembly, e.g. while arranging the adjusting member at the distal end portion of the cartridge holder 3. The adjusting member may comprise a needle hub 28. The outer surface of the needle hub 28 may be arranged completely outside of the cartridge holder 3. For arranging the needle hub 28 at the distal end portion of the cartridge holder 3, the needle hub 28 may be displaced in the proximal direction with respect to the cartridge holder 3 as indicated by arrow 31.

The needle hub 28 may comprise a set of engaging means 30. The engaging means may comprise guide lugs, for example. The engaging means 30 may be arranged at the proximal end portion of the needle hub 28. The engaging means 30 may be arranged along the needle hub 28. The engaging means 30 may extend axially.

The cartridge holder 3 may comprise a set of engaging means 29. Engaging means 29 may be arranged along an outer side of the cartridge holder 3. The engaging means 29 may extend axially. The engaging means 29 may comprise notches, for example. The engaging means 29 may be arranged at the distal end portion of the cartridge holder 3. The engaging means 29 may be arranged such that the dimension of the engaging means 29 is matched to the dimension of the engaging means 30 enabling that the needle hub 28 may be arrangeable and securable to the distal end portion of the cartridge holder 3. Mechanical cooperation of the engaging means 30, 29 may prevent the needle hub 28 from rotation with respect to the cartridge holder 3, when the engaging means 30 engage the cartridge holder 3.

The needle hub 28 may be permanently secured to the cartridge holder 3 for example by means of irradiation of engaging means 30 and engaging means 29 with a laser to form a laser-weld. Once the needle hub 28 is secured to the cartridge holder 3 the needle hub 28 may be prevented from axial displacement with respect to the cartridge holder 3. Once secured to the cartridge holder 3 the needle hub 28 may keep the distance between the distal portion of the cartridge 4 and the distal portion of the cartridge holder 3 as described above.

The cartridge 4 may be positioned in the proximal end position before securing the needle hub 28 to the distal portion of the cartridge holder 3. Alternatively, the needle hub 28 may be pushed proximally with respect to the cartridge holder 3, thereby proximally displacing the cartridge 4 towards the proximal end position until the piston 5 abuts the piston rod 6.

After having secured the needle hub 28 to the cartridge holder 3 the needle unit 37 may be attached to the needle hub 28.

FIG. 8 schematically shows an inner view of a part of the drug delivery device 1 of FIG. 1 for a fourth embodiment.

The adjusting member may comprise a needle insert 34. The distal portion of the cartridge 4 may comprise an outwardly directed shoulder portion 32. The distal portion of the cartridge holder 3 may comprise an inwardly directed flange portion 33. The shoulder portion 32 may be of suitable dimension to abut the flange portion 33. The needle insert 34 may prevent an abutment of the shoulder portion 32 and the flange portion 33, thereby keeping the distal portion of the cartridge 4 at a distance to the distal portion of the cartridge holder 3. The distance may depend from the gap 21 which is in the initial assembly state between the piston 5 and the piston rod 6.

For axially displacing the cartridge 4 in the proximal direction with respect to the cartridge holder 3 towards the proximal end position needle unit 37 (not explicitly shown in FIG. 8, see FIG. 3) may be releasably secured to the cartridge holder 3. Needle unit 37 may be securable to the cartridge holder 3 by means of engaging means 42 of the cartridge holder 3. Engaging means 42 may comprise an outer thread of the cartridge holder 3, for example.

While releasably securing the needle unit 37 to the cartridge holder 3a proximally directed force is exerted on the needle insert 34 as indicated by arrow 35. Due to the proximally directed force the needle insert 34 and hence, the cartridge 4 may be displaced in the proximal direction with respect to the cartridge holder 3 until the piston abuts the piston rod 6, e.g. until the cartridge 4 is in the proximal end position.

Afterwards the needle unit 37 and hence, the needle insert 34 may be releasable or irreversably secured to the cartridge holder 3, for example by applying force, adhesive or heat to engaging means 42, as described above, for keeping the cartridge 4 in the end position.

As the piston rod 6 abuts the piston 5 when the drug delivery device 1 is in the original supplied condition from the manufacturer no user-operated steps may be necessary for priming the drug delivery device 1. High dose accuracy of the drug delivery device 1 may be guaranteed and underdosing, which may have fatal or lethal consequences for the user, may be prevented.

The drug delivery device 1 may for example be configured for setting and delivering doses of 30 IU or greater, for example a dose of 50 IU or greater, thereby providing high dose accuracy. Alternatively, the drug delivery device 1 may provide for doses of 5 IU or less or any dose in-between while having good dose accuracy.

Other implementations are within the scope of the following claims. Elements of different implementations may be combined to form implementations not specifically described herein.

REFERENCE NUMERALS

1 Drug delivery device
2 Housing
3 Cartridge holder
4 Cartridge
5 Piston
6 Piston rod
7 Distal end
8 Proximal end
9 Septum
10 Drug
11 Dose member
12 Needle hub
13 Outer thread
14 Engaging means
15 Dose button
16 Inner thread
17 Needle
18 Needle holder
19 Cap
20 Bearing member
21 Gap
22 Arrow
23 Connection region
24 Engaging means
25 Needle insert
26 Engaging means
27 Connection region
28 Needle hub
29 Engaging means
30 Engaging means
31 Arrow
32 Shoulder portion
33 Flange portion
34 Adjusting member
35 Arrow
36 Outer surface
37 Needle unit
38 Outlet
39 Aperture
40 Threaded connection
41 Drive mechanism
42 Engaging means

The invention claimed is:

1. A method for securing a cartridge in a cartridge holder of a drug delivery device, wherein the drug delivery device is configured to dispense at least one dose of a drug, the method comprising the following steps:

providing the cartridge comprising a piston, wherein a distal portion of the cartridge comprises an outwardly directed shoulder portion, inserting the cartridge into the cartridge holder, the cartridge holder comprising a proximal end and a distal end, wherein a distal portion of the cartridge holder comprises an inwardly directed flange portion, the shoulder portion of the cartridge being suitable dimension to abut the flange portion of the cartridge holder, prior to dose dispense, utilizing an adjusting member to axially displace the cartridge in a proximal direction with respect to the cartridge holder from a distal initial position to a proximal end position, so as to reduce a gap between a piston rod and the piston of the cartridge, utilizing the adjusting member to secure the cartridge in the proximal end position against displacement in a distal direction with respect to the cartridge holder, and preventing an abutment of the shoulder portion of the cartridge and the flange portion of the cartridge holder, wherein the adjusting member is used for securing the cartridge in the cartridge holder and wherein securing the cartridge in the cartridge holder comprises securing the adjusting member against displacement with respect to the cartridge holder in the distal direction when the cartridge is in the proximal end position, and wherein the adjusting member extends from an inside of the cartridge holder to an outside of the cartridge holder, wherein an outer surface of the adjusting member accessible from the outside of the cartridge holder is provided for attaching a needle unit to the adjusting member.

2. The method of claim 1, wherein the adjusting member is displaced in the proximal direction with respect to the cartridge holder for axially displacing the cartridge.

3. The method according to claim 2, wherein the adjusting member is reversibly fixed to the cartridge holder.

4. The method according to claim 1, wherein the outer surface of the adjusting member is threaded.

5. The method according to claim 1, wherein the adjusting member comprises an outer thread which engages an inner thread of the cartridge holder, thereby securing the adjusting member to the cartridge holder.

6. A method for assembling a drug delivery device, comprising the steps of:

providing a cartridge containing a drug, a piston being retained within the cartridge, providing a cartridge holder, providing a housing, a piston rod being retained in the housing, the piston rod being operable to displace the piston with respect to the cartridge, securing the cartridge holder to the housing, such that the piston is arranged at a distance from the piston rod, securing the cartridge in the cartridge holder according to the method of claim 1, wherein, when the cartridge is axially displaced in the proximal direction with respect to the cartridge holder away from an initial position, the piston is displaced towards the piston rod.

7. The method according to claim 6, comprising the step of, during an axial displacement of the cartridge with respect to the cartridge holder, detecting whether the piston abuts the piston rod and, if so, stopping the axial displacement of the cartridge with respect to the cartridge holder in a proximal end position and securing the cartridge against displacement in a distal direction with respect to the cartridge holder.

8. The method according to claim 6, wherein the cartridge has an outlet at its distal end, a septum sealing the outlet, and wherein the piston seals the cartridge proximally.

* * * * *